(12) United States Patent
Batchelor et al.

(10) Patent No.: US 9,089,337 B2
(45) Date of Patent: Jul. 28, 2015

(54) ELECTROSURGICAL SYSTEM HAVING GRASPER AND SNARE WITH SWITCHABLE ELECTRODE

(71) Applicant: GYRUS ACMI, INC., Southborough, MA (US)

(72) Inventors: Kester Batchelor, Mound, MN (US); Tracey Dobbs, Delano, MN (US); Jyue Boon Lim, New Brighton, MN (US); Nikhil Murdeshwar, Maple Grove, MN (US); Tsuyoshi Hayashida, Maple Grove, MN (US)

(73) Assignee: GYRUS ACMI, INC., Southborough, MA (US)

( * ) Notice: Subject to any disclaimer, the term of this patent is extended or adjusted under 35 U.S.C. 154(b) by 13 days.

(21) Appl. No.: 14/074,202

(22) Filed: Nov. 7, 2013

(65) Prior Publication Data

US 2015/0126998 A1      May 7, 2015

(51) Int. Cl.
*A61B 18/18*      (2006.01)
*A61B 18/14*      (2006.01)
*A61B 18/12*      (2006.01)

(52) U.S. Cl.
CPC ............. *A61B 18/14* (2013.01); *A61B 18/1442* (2013.01); *A61B 2018/124* (2013.01); *A61B 2018/141* (2013.01); *A61B 2018/1407* (2013.01)

(58) Field of Classification Search
CPC .. A61B 18/1402; A61B 10/06; A61B 17/221; A61B 17/32056; A61B 2017/00269; A61B 2017/00353; A61B 2017/2215; A61B 2018/1407

USPC .......................................................... 606/48
See application file for complete search history.

(56) References Cited

U.S. PATENT DOCUMENTS

| | | | |
|---|---|---|---|
| 4,493,320 A | 1/1985 | Treat | |
| 4,905,691 A | 3/1990 | Rydell | |
| 5,472,442 A * | 12/1995 | Klicek | 606/42 |
| 6,113,596 A | 9/2000 | Hooven et al. | |
| 6,610,056 B2 | 8/2003 | Durgin et al. | |
| 7,083,616 B2 | 8/2006 | Kawai et al. | |
| 2006/0025780 A1 * | 2/2006 | James | 606/110 |
| 2012/0016190 A1 | 1/2012 | Yanuma et al. | |

FOREIGN PATENT DOCUMENTS

| | | | | |
|---|---|---|---|---|
| JP | 05184589 A * | 7/1993 | | A61B 17/36 |
| JP | A-05-184589 | 7/1993 | | |
| JP | A-2003-135378 | 5/2003 | | |

* cited by examiner

*Primary Examiner* — Joseph Stoklosa
*Assistant Examiner* — Amanda Zink
(74) *Attorney, Agent, or Firm* — Oliff PLC

(57) ABSTRACT

An electrosurgical system includes a grasper and a snare that each includes electrodes. The grasper includes a first electrode that is attachable to a first output of an energy supply. The snare includes a second electrode that is attachable to a second output of the energy supply. When the first and second electrodes are coupled to the energy supply, the grasper and snare operate as a bipolar electrosurgical system. By grasping the tissue with the jaws of the grasper, the current path between the electrode on the snare and the electrode on the grasper is relatively short, and thus the system operates like a bipolar electrosurgical system. Accordingly, the applied energy can be focused to a small area, minimizing damage to surrounding tissue. In addition, energy suitable for coagulating the cut portion of the stalk of the removed tissue can be readily applied with the bipolar electrosurgical system.

2 Claims, 5 Drawing Sheets

ELECTROSURGICAL SYSTEM HAVING GRASPER AND SNARE WITH SWITCHABLE ELECTRODE

BACKGROUND

This disclosure relates to systems for removing tissue from patients, and is particularly useful for removing pedunculated tissue structures such as polyps and pedunculated uterine fibroids.

Uterine fibroids are the most common pelvic tumor in women, affecting approximately one quarter of women during their reproductive years. Uterine fibroids are generally noncancerous, but may potentially lead to infertility or cause adverse effects if they occur during pregnancy. Typical symptoms include abnormal bleeding, pressure, or pain.

Uterine fibroids are categorized based on location on the uterus. Sub-mucosal fibroids form on the inside wall of the uterus; sub-serosal fibroids form on the outside wall of the uterus; intra-mural fibroids form within the wall of the uterus; and pedunculated fibroids are connected to the inside or outside wall of the uterus by a stalk.

Currently uterine fibroid treatments include both pharmaceutical and surgical techniques. Pharmaceutical treatments often do not adequately treat the symptoms of uterine fibroids, ultimately necessitating surgical intervention. Surgical techniques include hysterectomy, myomectomy, endometrial ablation, myolysis and uterine artery occlusion. In addition, interventional radiology and high frequency focused ultrasound techniques exist for the treatment of uterine fibroids.

All of these treatment techniques suffer from shortcomings, such as the risk of relapse, infertility, and applicability to only one or a few types of uterine fibroids.

SUMMARY

One might use an electrosurgical snare to remove pedunculated fibroids from a uterine wall. The snare could include an electrode that is used in conjunction with a patch electrode that is attachable to a surface of a patient in order to apply monopolar energy to the fibroid in order to remove the fibroid. In particular, the snare is placed around the stalk of the fibroid and then tightened to grasp the stalk. Then, monopolar energy is applied in order to cut the stalk.

The use of monopolar energy, however, may not be the best electrosurgical mode in all cases because, with the patch electrode provided on a surface of the patient, energy is transmitted through portions of the patient, and can damage the patient's tissue. The electrical return path from the snare to the return pad can be unpredictable and, due to the distance of travel through the body, may require high voltages. Also, poor adhesion of the patch to the patient's skin can cause burning of the patient's skin due to increased current density at the still-adhered portion of the patch. In addition, although monopolar energy is suited for cutting, it may not be effective at coagulating the site where the fibroid was cut from the stalk.

Although embodiments of the invention will be described in conjunction with the removal of pedunculated fibroids, the invention is applicable to the removal of other tissue, for example, polyps.

In accordance with some embodiments, an electrosurgical system includes a grasper and a snare that each include electrodes. The grasper includes jaws that are movable relative to each other between an open condition and a closed condition so as to be capable of grasping tissue. Amputation of the fibroid by the snare is benefited by use of the grasper to contain the amputated tissue. The grasper includes a first electrode that is attachable to a first output of an energy supply. The snare includes a second electrode that is attachable to a second output of the energy supply. The first and second outputs typically have opposite polarities. When the first and second electrodes are coupled to the energy supply, the grasper and snare operate as a bipolar electrosurgical system. By grasping the tissue (e.g., polyp or fibroid) with the jaws of the grasper, which are in close proximity to the snare, the current path between the electrode on the snare and the electrode on the grasper is relatively short, and thus the system operates like a bipolar electrosurgical system. In this way, this configuration differs from a traditional monopolar snare. Electrical energy is supplied by the snare to the base of the fibroid, but instead of being conducted by a potentially unpredictable path through the body to a return pad, the electrical energy is conducted to the grasper at the end of the fibroid. Any inadvertent injury to this tissue is significantly less disadvantageous because such injury would be limited to the tissue that is being amputated. Accordingly, the applied energy can be focused to a small area (the stalk of the polyp or fibroid), minimizing damage to surrounding tissue.

According to one embodiment, the system is a static system in that the connection of the first electrode to the first output of the energy supply and the connection of the second electrode to the second output of the energy supply are fixed.

According to other embodiments, switching circuitry can be provided between at least one of the electrodes and the energy supply so that the system can be switched between various configurations.

According to some embodiments, the system further includes switching circuitry that selectively couples the second electrode (associated with the snare) to the second output of the energy supply, with the switching circuitry being switchable between at least first and second positions. The switching circuitry couples the second electrode to the second output of the energy supply when in the first position to enable the grasper and the snare to operate as the bipolar electrosurgical system. The switching circuitry disconnects the second electrode from the second output of the energy supply and connects the second output of the energy supply to a third electrode when the switching circuitry is in the second position.

According to some embodiments, the first and third electrodes are disposed on respective first and second jaws of the grasper so that the grasper operates as a bipolar grasper when the switching circuitry is in the second position. This configuration is well suited to performing coagulation with the grasper.

According to other embodiments, the system includes a patch electrode that is attachable to a surface of a patient, and the patch electrode includes the third electrode. In such a configuration, the grasper operates as a monopolar grasper when the switching circuitry is in the second position.

In some embodiments, the switching circuitry includes a third position such that (i) when in the first position, the grasper and the snare operate as the bipolar electrosurgical system, (ii) when in the second position, the grasper operates as a bipolar grasper, and (iii) when in the third position, the grasper operates as a monopolar grasper, with the second output of the power supply being connected to the patch electrode.

According to some embodiments, the electrosurgical system includes switching circuitry that selectively couples the first electrode (of the grasper) to the first output of the energy supply, and the switching circuitry is switchable between at least first and second positions. The switching circuitry couples the first electrode to the first output of the energy supply when in the first position to enable the grasper and the snare to operate as the bipolar electrosurgical system. The switching circuitry disconnects the first electrode from the first output of the energy supply, and connects the first output of the energy supply to a third electrode when in the second position. When the third electrode is a patch electrode that is attachable to a surface of the patient, the snare operates as a monopolar snare when the switching circuitry is in the second position.

BRIEF DESCRIPTION OF THE DRAWINGS

Exemplary embodiments will be described in detail with reference to the following drawings in which.

DETAILED DESCRIPTION OF THE EMBODIMENTS

The following exemplary embodiments are described below with reference to the figures in the context of uterine fibroid treatment, and in particular removal of pedunculated uterine fibroids. However, the disclosed electrosurgical system is not limited to use for removing pedunculated fibroids. The system is suitable for removing various pedunculated tissue structures such as, for example, polyps located, for example, in the gastro-intestinal tract. Thus, although the following description is primarily focused on the removal of pedunculated uterine fibroids, other pedunculated tissue structures can be removed with the disclosed system.

Figure 1:
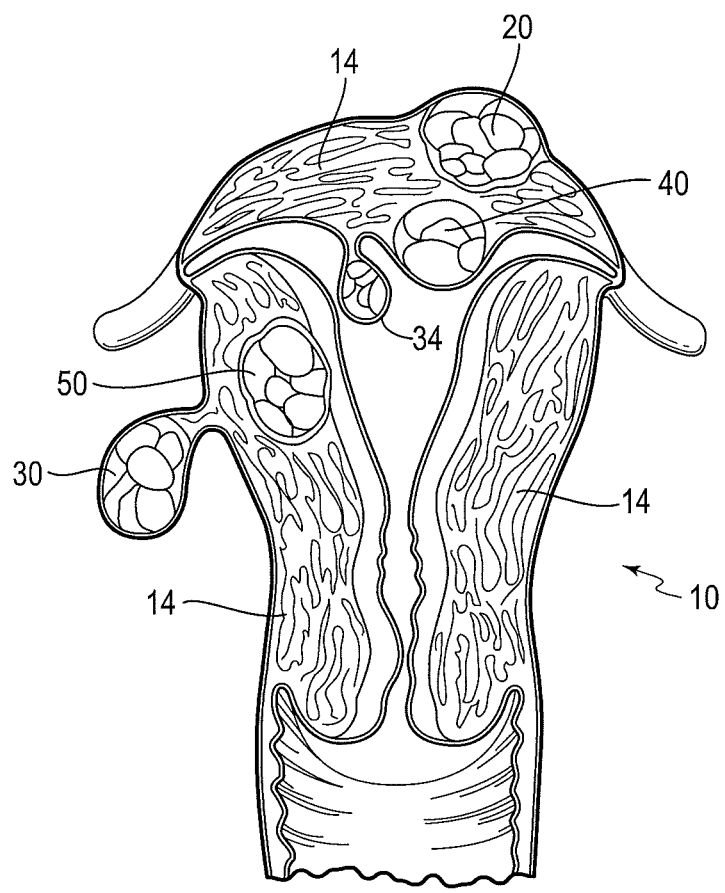
FIG. 1 illustrates various locations of uterine fibroids.

FIG. 1 illustrates different anatomical locations of uterine fibroids that can potentially afflict a patient. A sub-mucosal fibroid 40 is located on the inside wall of the uterus 10. A sub-serosal fibroid 20 is located on the outside wall of the uterus 10. An intra-mural fibroid 50 is located within the wall 14 of the uterus 10. A pedunculated fibroid 30 is attached to the outer wall of the uterus 10. Because it is attached to the outer wall of the uterus 10, fibroid 30 more specifically is known as a pedunculated sub-serosal fibroid. Fibroid 34 is known as a pedunculated sub-mucosal fibroid because it is attached to the inner wall of the uterus 10.

The location of a patient's fibroid(s) is first determined by one or more known imaging techniques. For example, ultrasonic imaging (known as "ultrasound") can be performed using a transducer placed externally of the patient's body or located within the uterus, for example, at the end of a transcervically inserted ultrasonic probe. MRI also could be used. Such technologies also can be used to locate polyps.

Once the location of the (or each) fibroid has been determined, the surgeon will determine how to access the fibroid(s). For example, pedunculated sub-mucosal fibroids typically are accessed transcervically, whereas pedunculated sub-serosal fibroids typically are accessed from the pelvic cavity (i.e., laparoscopically accessed). However, the manner of accessing each fibroid also depends on the desired outcome of the surgery (e.g., fertility, resolution of the patient's symptoms, etc.), the size of each fibroid, as well as the location of other fibroids within the uterus.

Once the electrosurgical device has been inserted into the patient, the patient's uterus (or GI tract) is manipulated into position to present the fibroid (or polyp) for treatment. The snare of the device then is looped around the fibroid (or a polyp) and tightened to occlude the stalk of the pedunculated fibroid (or polyp). In addition, the grasper is actuated so that it grasps the fibroid (or polyp). The snare and grasper then are electrically activated to excise the fibroid (or polyp). The snare and grasper together function as a bipolar electrosurgical system. The electrode on the grasper is designed so that the energy is concentrated at the snare, which cuts through the stalk of the pedunculated tissue structure (e.g., fibroid or polyp). In particular, because it is the current density that gives rise to heat, configuring the snare and the grasper so that the snare has less electrically conductive surface area in contact with the tissue than does the grasper causes the current density at the snare to be higher (that is, more focused) so that the cutting occurs at the snare and not at the grasper. Thus, the surface area of the electrically conductive portion of the grasper that contacts the tissue should be larger than the surface area of the electrically conductive portion of the snare that contacts the tissue by an amount that is sufficient to cause the energy to be focused at the snare so that the snare will ablate (cut) the stalk of the fibroid (or polyp), thereby amputating the fibroid or polyp. The excised fibroid or polyp held by the grasper is then extracted from the patient.

Figure 2:
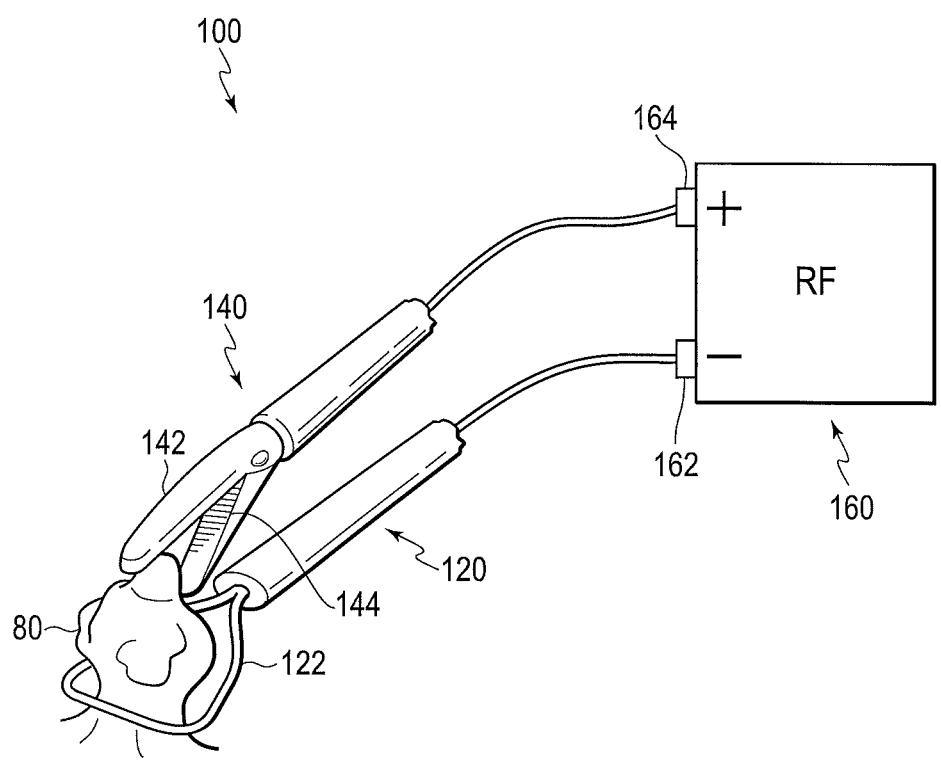
FIG. 2 is a diagram of an electrosurgical system (a pedunculated tissue structure removal system) according to one embodiment of the invention.

An electrosurgical assembly (pedunculated tissue structure removal assembly or system) 100 according to one embodiment of the invention is shown in FIG. 2. FIG. 2 shows the most basic system in which a grasper 140 and a snare 120 are coupled to the outputs of a generator (bipolar energy source) 160. The FIG. 2 system is considered to be a "static" system in that during operation, the electrical connections between the energy source 160 and the grasper 140 and snare 120 remain fixed (no switching occurs).

In the FIG. 2 embodiment, the snare 120 includes a wire loop 122 that is electrically conductive and can be tightened around the stem of a pedunculated tissue structure 80 such as a fibroid or polyp. The proximal end of the loop 122 is electrically connected to one output (in FIG. 2, the return output) 162 of the energy source 160. Some examples of electrosurgical snares having electrically-conductive loops that can be moved between loosened and tightened positions by a pulling member, and that can be coupled to an energy source, are shown in U.S. Pat. No. 4,493,320, U.S. Pat. No. 4,905,691 and U.S. Pat. No. 6,610,056, the disclosures of which are incorporated herein by reference in their entireties.

The grasper 140 can be any type of grasper that is capable of affixing itself to tissue. In the preferred embodiment, grasper 140 includes two grasping members or jaws 142, 144. One or both of the jaws 142, 144 can be electrically conductive and one or both of them are electrically connected to another output (in FIG. 2, the active output) 164 of the energy supply 160. An example of an electrosurgical grasper having movable jaws, and that can be coupled to an energy source, is shown in U.S. Pat. No. 7,083,616, the disclosure of which is incorporated herein by reference in its entirety.

During use, after the surgeon tightens the loop 122 of the snare 120 around the stalk of the pedunculated tissue structure 80, the surgeon then grasps the tissue structure 80 with the jaws 142, 144 of the grasper 140. One or both of the jaws 142 and 144 can be movable so that the jaws are movable toward and away from each other. The jaws 142, 144 can be spring biased toward each other so that they will grasp tissue without the surgeon needing to apply any force to the grasper. Once the loop 122 is tightened and the tissue structure 80 is held by the grasper 140, the surgeon presses a button either on the generator or on a handpiece (the handpiece can be of the snare 120, the grasper 140 or of a device such as a cannula through which each of the snare 120 and grasper 140 is introduced into the body) so as to cause an energy signal to be supplied through the active output 164 and through one or both of the jaws 142, 144 of the grasper 140. Because the area of the surface of the loop 122 which contacts the tissue 80 is smaller than the area of the tongs 142, 144 which contacts the tissue 80, the current is concentrated at the loop 122 so that the stalk of the tissue is cut, thereby separating the pedunculated tissue structure 80 from the patient. That is, as explained previously, the current density is greater at the loop than at the grasper so that the tissue effects related to current, including ablation, are greater at the loop than at the grasper, so that the stalk is cut. It is, of course, possible to attach the loop 122 to the active output 164 of the energy supply 160 and to attach the grasper 140 to the return output 162 of the energy supply 160. In this regard, it should be noted that the words "active" and "return" do not have the same meaning when describing a monopolar system versus a bipolar system. In a monopolar system, the "return" electrode and generator terminal more accurately are "returns" in that they are used to return current that has been applied by the active electrode (and terminal) back to the generator. In a bipolar system, the two poles (and thus the electrodes and terminals) oscillate their voltage with respect to each other. At one moment in time one pole (say, the snare) has a positive (+) polarity and the other (grasper) has a negative (−) polarity. But halfway through the AC cycle, this has inverted and the snare is negative (−) and he grasper is positive (+). Since the generator can operate as a monopolar source or as a bipolar source, one of the terminals has been labeled with (+) and the other with (−), to show which terminal would be coupled to the electrode that functions as a return when in a monopolar operating mode.

Because the loop 122 and the jaws 142, 144 are made of an electrically-conductive material, current will be conducted through the electrical circuit formed by energy source 160, the grasper 140, the snare 120 and the tissue disposed between and contacted by the jaws 142/144 and the loop 122. However, it also is possible to provide specific electrodes on one or both of the jaws 142, 144 and on the loop 122 that are electrically connected to terminals provided adjacent to the proximal ends of the grasper 140 and the snare 120, respectively, by electrically-conductive traces or wires on the grasper 140 and on the snare 120. This enables precise control of the size of the electrode area that will contact the tissue.

Because the jaws of the grasper and the loop of the snare are very close to each other, the assembly including the grasper 140 and snare 120 functions as a bipolar system. Accordingly, less energy is required to perform cutting and coagulation than would be needed in a monopolar system in which the return electrode is a patch disposed on the patient's body. As described earlier, a bipolar system also is more efficient and less traumatic than a monopolar system.

The embodiments shown in FIGS. 3-7 incorporate switching circuitry so that the system is even more flexible. The switching circuitry is controlled by a button or switch provided on the handpiece described above, or on the energy source 160.

Figure 3:
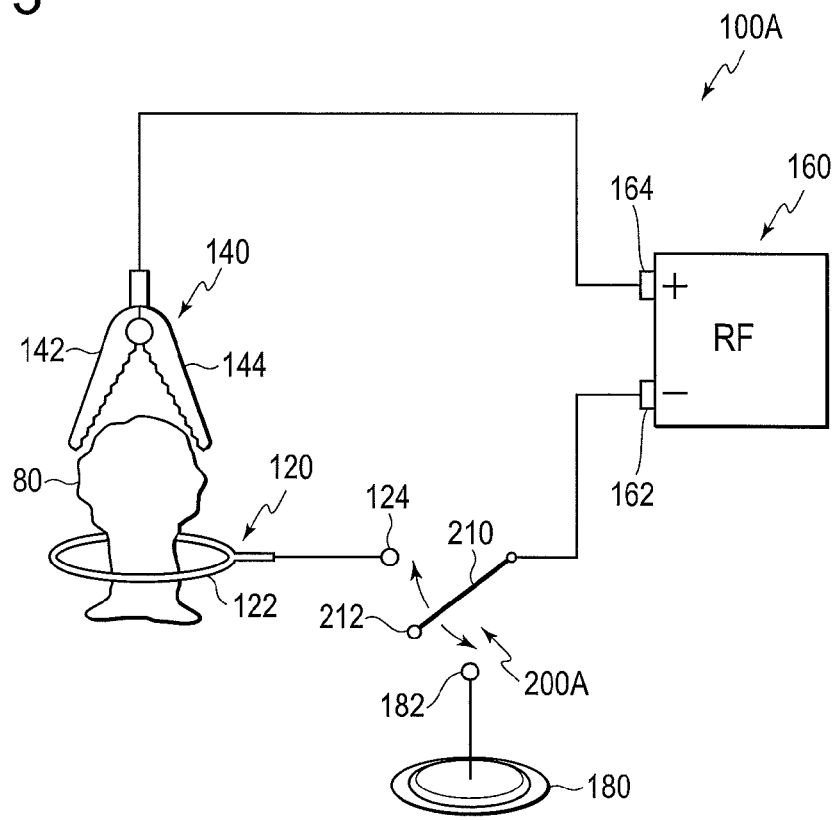
FIG. 3 is a diagram of an electrosurgical system according to a second embodiment of the invention.

FIG. 3 shows an electrosurgical assembly 100A that is similar to the assembly 100 of FIG. 2 except that switching circuitry 200A is provided between the snare 120 and the return output 162 of the energy source 160. In addition, a patch electrode 180 is provided for attachment to the skin of the patient near the site of the surgery. The switching circuitry 200A of FIG. 3 includes a movable switch 210 by which the return output 162 of the energy source can be alternately attached to either the snare 120 or the patch electrode 180. Movable switch 210 includes a terminal 212 that contacts terminal 124 of the snare 120 when the switch 210 is in a first position. The terminal 212 of the switch 210 contacts a terminal 182 attached to the patch electrode 180 when the switch 210 is in a second position. When the switch 210 is in the first position such that terminal 212 contacts the terminal 124 of the snare 120, the grasper 140 and the snare 120 operate as a bipolar electrosurgical system as described above with respect to the FIG. 2 embodiment. When the terminal 212 of the switch 210 contacts the terminal 182 of the patch electrode, the grasper 140 and the patch electrode 180 function as a monopolar system, with energy being applied to the grasper 140 via active output 164, and energy being returned through patch electrode 180. The grasper could be used to perform coagulation at the site where the tissue structure 180 was removed.

Figure 6:
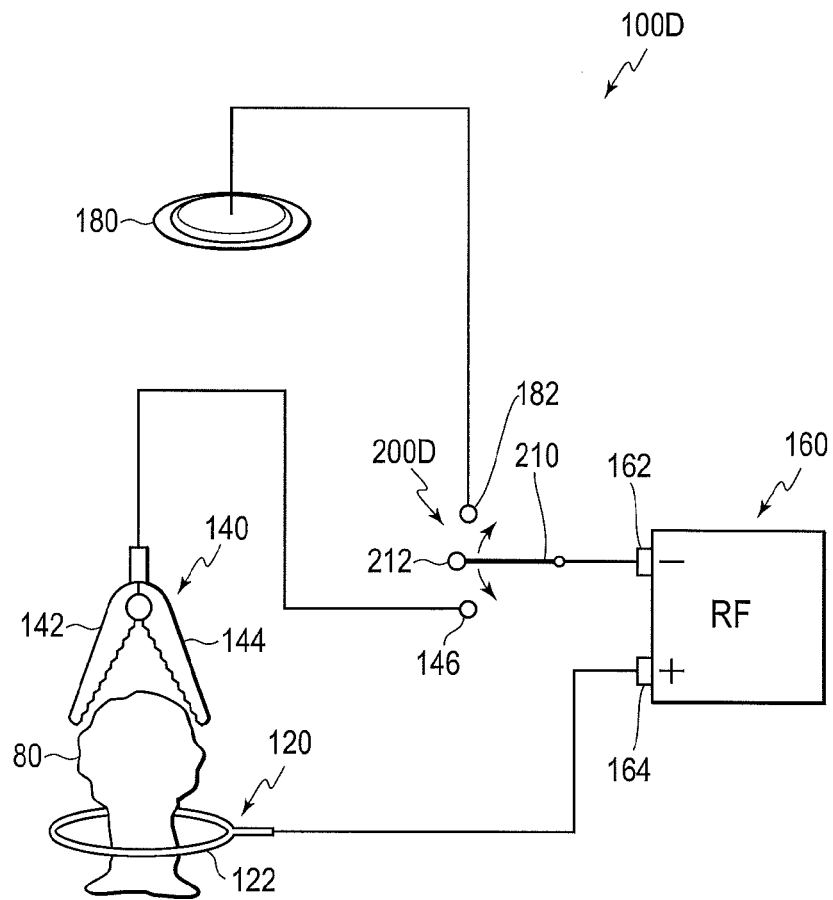
FIG. 6 is a diagram of an electrosurgical assembly according to a fifth embodiment of the invention.

The electrosurgical assembly 100D shown in the embodiment of FIG. 6 is similar to the embodiment of FIG. 3 except that the switching circuitry 200D is provided between the grasper 140 and the return output 162 of the energy source 160, instead of on the line associated with the snare 120. Accordingly, in the FIG. 6 embodiment, when the switch 210 is in a first position such that the terminal 212 contacts a terminal 146 of the grasper 140, the grasper 140 and the snare 120 operate as a bipolar electrosurgical system. When the switch 210 is placed in a second position at which the terminal 212 contacts the terminal 182 of the patch electrode 180, the snare 120 and the patch electrode 180 function as a monopolar system by which energy can be applied to tissue through the loop 122 of the snare 120, with the energy being received at the patch electrode 180. Thus, the loop 122 can be used to apply monopolar energy and perform coagulation at the site of tissue removal.

Figure 4:
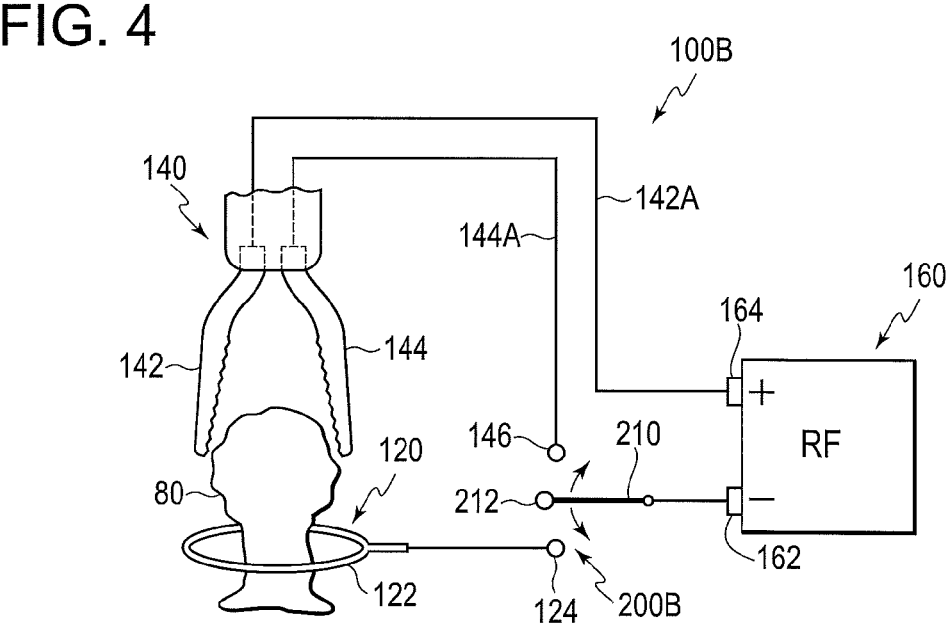
FIG. 4 is a diagram of an electrosurgical system according to a third embodiment of the invention.

FIG. 4 shows a third embodiment 100B in which a separate electrode is provided for each of the jaws 142, 144 of the grasper 140. Jaw 142 of the grasper 140 is attached to the active output 164 of the energy source 160 via conductive line 142a. The jaw 144 has a conductive line 144a with the terminal 146 at its proximal end. The terminal 146 can be selectively attached to the return output 162 of the energy source 160 via switch 210 of switching circuitry 200B. When switch 210 is in a first position, terminal 212 contacts terminal 124 such that the grasper 140 and the snare 120 operate as a bipolar electrosurgical assembly. When the switch 210 is moved to a second position at which the terminal 212 contacts terminal 146 of jaw 144, the grasper functions as a bipolar grasper. The bipolar grasper can be used, for example, to perform coagulation of the tissue site after the tissue 80 has been removed.

Figure 5:
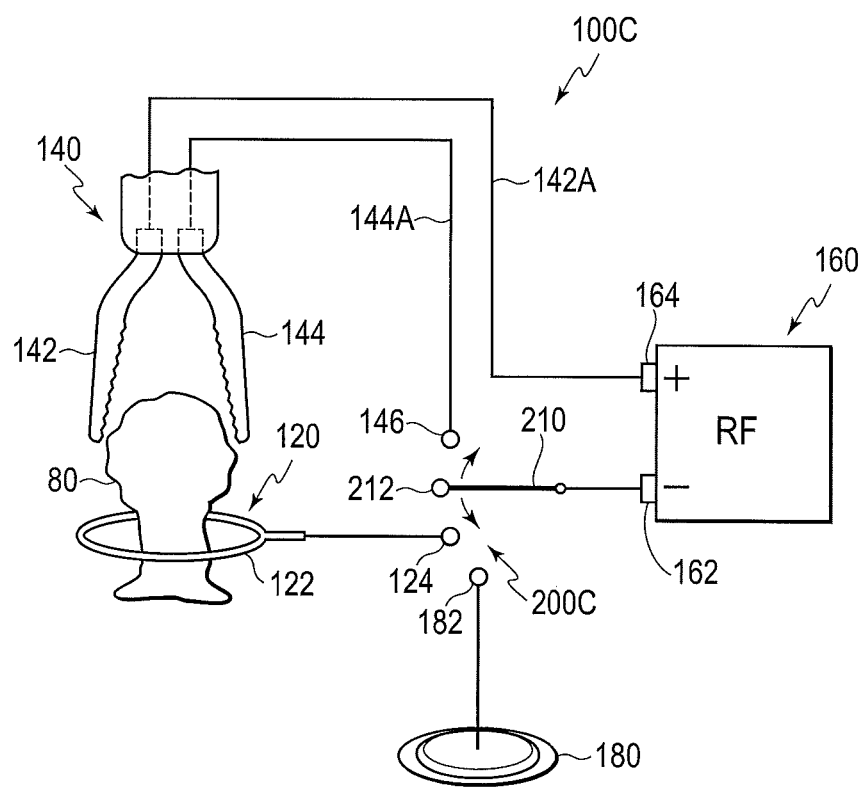
FIG. 5 is a diagram of an electrosurgical assembly according to a fourth embodiment of the invention.

FIG. 5 shows a fourth embodiment 100C that is a modification of the third embodiment whereby a patch electrode 180 is added to the system and the switching circuitry 200C includes a switch 210 having three positions. Like the third embodiment, a separate electrode is provided for each of the jaws 142, 144 of the grasper 140. Jaw 142 of the grasper 140 is attached to the active output 164 of the energy source 160 via conductive line 142a. The jaw 144 has a conductive line 144a with the terminal 146 at its proximal end. The terminal 146 can be selectively attached to the return output 162 of the energy source 160 via switch 210 of switching circuitry 200C. When switch 210 is in a first position, terminal 212 contacts terminal 124 of the loop 122 such that the grasper 140 and the snare 120 operate as a bipolar electrosurgical assembly. When the switch 210 is moved to a second position at which the terminal 212 contacts terminal 146 of jaw 144, the grasper functions as a bipolar grasper. The bipolar grasper can be used, for example, to perform coagulation of the tissue site after the tissue 80 has been removed. When the switch 210 is placed in a third position at which the terminal 212 contacts the terminal 182 of the patch electrode 180, the grasper 140 and the patch electrode 180 function as a monopolar system by which energy can be applied to tissue through the jaw 142 of the grasper 140, with the energy being received at the patch electrode 180. Thus, the grasper 140 can be used to apply monopolar energy and perform coagulation at the site of tissue removal.

Figure 7:
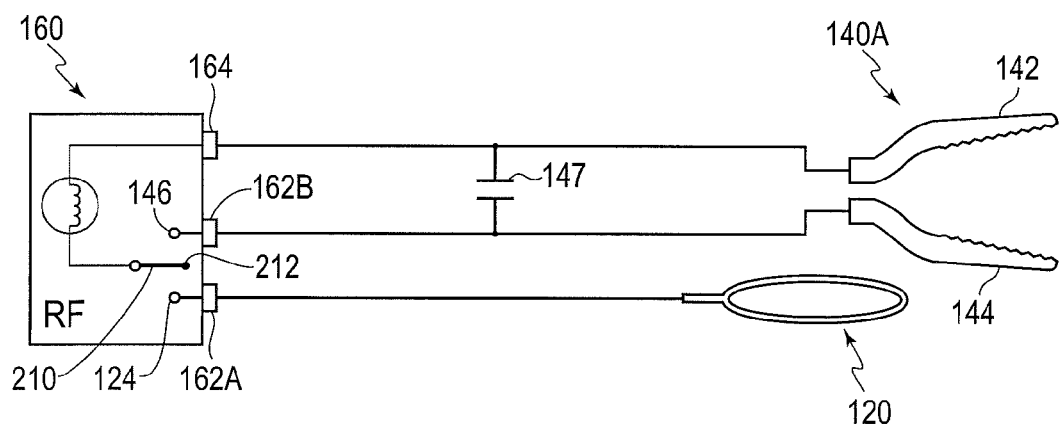
FIG. 7 is a diagram of an electrosurgical assembly according to embodiments of the invention using an alternative grasper structure.

FIG. 7 shows a modified grasper 140A that can be used in the embodiments in which each jaw of the grasper has (or functions as) a separate electrode. A capacitor 147 is provided between the jaws 142 and 144. The capacitor should be capable of withstanding a relatively high voltage (for example, about 1000 V) and have an impedance of, for example, 1 nF. The capacitor allows a small amount of energy to pass therethrough between the signal lines of the jaws 142 and 144, but most of the energy will pass through the tissue disposed between the jaws 142 and 144 when the switch 210 is in the position at which the terminal 212 contacts the terminal 146 of the jaw 144. When the switch is in this position (contacting the terminal 146), the grasper 140 functions as a bipolar grasper and can perform coagulation. When the switch 210 is in the position at which the terminal 212 contacts the terminal 124 of the snare 120, the snare 120 and the grasper 140 function as a bipolar system and can perform cutting. During cutting, the two jaws 142 and 144 are effectively linked via the capacitor 147. Because the switch 210 is provided within the energy source 160, the energy source effectively has two return outputs 162a and 162b.

The illustrated exemplary embodiments are intended to be illustrative and not limiting. Various changes may be made without departing from the spirit and scope of the invention.

What is claimed is:

1. An electrosurgical system comprising:
    a grasper having a first jaw and a second jaw that are movable relative to each other between an open condition and a closed condition so as to be capable of grasping tissue, the grasper including a first electrode disposed on the first jaw and that is attachable to a first output of an energy supply, the grasper including a third electrode disposed on the second jaw and that is selectively attachable to a second output of the energy supply, the third electrode is electrically isolated from the first electrode;
    a snare having a second electrode that is selectively attachable to the second output of the energy supply; and
    switching circuitry that selectively couples the second electrode or the third electrode to the second output of the energy supply, the switching circuitry being switchable between at least first and second positions, (i) the switching circuitry coupling the second electrode to the second output of the energy supply when in the first position to enable the grasper and the snare to operate as a bipolar electrosurgical system, and (ii) the switching circuitry disconnecting the second electrode from the second output of the energy supply when in the second position and coupling the second output of the energy supply to the third electrode when in the second position so that the grasper operates as a bipolar grasper when the switching circuitry is in the second position.

2. The electrosurgical system according to claim 1, further comprising:
    a patch electrode that is attachable to a surface of a patient, wherein the switching circuitry is switchable to a third position, the switching circuitry coupling the second output of the energy supply to the patch electrode so that the grasper operates as a monopolar grasper when the switching circuitry is in the third position.

* * * * *